(12) United States Patent
Bischoff et al.

(10) Patent No.: US 8,858,540 B2
(45) Date of Patent: Oct. 14, 2014

(54) OPHTHALMOLOGICAL LASER TREATMENT DEVICE

(75) Inventors: Mark Bischoff, Jena (DE); Gregor Stobrawa, Jena (DE)

(73) Assignee: Carl Zeiss Meditec AG, Jena (DE)

( * ) Notice: Subject to any disclaimer, the term of this patent is extended or adjusted under 35 U.S.C. 154(b) by 0 days.

(21) Appl. No.: 13/635,999

(22) PCT Filed: Mar. 17, 2011

(86) PCT No.: PCT/EP2011/001319
§ 371 (c)(1),
(2), (4) Date: Nov. 16, 2012

(87) PCT Pub. No.: WO2011/116900
PCT Pub. Date: Sep. 29, 2011

(65) Prior Publication Data
US 2013/0072916 A1  Mar. 21, 2013

(30) Foreign Application Priority Data
Mar. 20, 2010 (DE) .......... 10 2010 012 616

(51) Int. Cl.
A61B 18/18 (2006.01)
A61F 9/008 (2006.01)

(52) U.S. Cl.
CPC .......... *A61F 9/00827* (2013.01); *A61F 9/008* (2013.01)
USPC ..................... 606/4; 606/5; 606/6

(58) Field of Classification Search
USPC ....................... 606/4, 5, 6
See application file for complete search history.

(56) References Cited

U.S. PATENT DOCUMENTS

| | | | |
|---|---|---|---|
| 5,620,436 A * | 4/1997 | Lang et al. .................. | 606/4 |
| 5,801,807 A | 9/1998 | Satake et al. | |
| 6,267,756 B1 | 7/2001 | Feuerstein et al. | |
| 6,986,765 B2 * | 1/2006 | Sumiya et al. .............. | 606/10 |
| 7,261,415 B2 | 8/2007 | Chernyak | |
| 2003/0163122 A1 | 8/2003 | Sumiya | |
| 2005/0278004 A1 | 12/2005 | Steinert et al. | |
| 2006/0116668 A1 * | 6/2006 | Gray et al. .................. | 606/10 |
| 2006/0155265 A1 | 7/2006 | Juhasz et al. | |
| 2007/0055222 A1 * | 3/2007 | Hohla et al. ................ | 606/12 |
| 2010/0026956 A1 | 2/2010 | Bischoff et al. | |
| 2011/0118609 A1 * | 5/2011 | Goldshleger et al. ........ | 600/476 |

FOREIGN PATENT DOCUMENTS

| | | |
|---|---|---|
| DE | 10 2007 060 008 | 6/2009 |
| WO | WO 2006/044056 | 4/2006 |
| WO | WO 2006/051364 | 5/2006 |
| WO | WO 2008/055604 | 5/2008 |
| WO | WO 2008/064771 | 6/2008 |
| WO | WO 2009/080790 | 7/2009 |

OTHER PUBLICATIONS

International Search Report(PCT/EP2011/001319) dated Jul. 12, 2011.

\* cited by examiner

*Primary Examiner* — Lynsey Crandall
*Assistant Examiner* — Sebastian X Lukjan
(74) *Attorney, Agent, or Firm* — Frommer Lawrence & Haug LLP

(57) ABSTRACT

An evaluating unit which is adapted to determine a degree of an instantaneous overlap between an optical zone of the eye and the structure, or at least a part of the structure effecting refractive correction, based on a recorded image. By determining the degree of overlap between the instantaneous optical zone and the structure to be introduced, it is possible to control the superposition of the optical zone with the tissue volume which is specifically altered by means of the laser cutting and, accordingly, to enable a maximum coverage.

22 Claims, 3 Drawing Sheets

OPHTHALMOLOGICAL LASER TREATMENT DEVICE

The present application claims priority from PCT Patent Application No. PCT/EP2011/001319 filed on Mar. 17, 2011, which claims priority from German Patent Application No. DE 10 2010 012 616.0 filed on Mar. 20, 2010, the disclosures of which are incorporated herein by reference in their entirety.

BACKGROUND OF THE INVENTION

Field of the Invention

The invention is directed to an opthalmological laser treatment device having a treatment laser, particularly an excimer laser or a femtosecond laser, for introducing energy into a portion of an eye of a patient according to a predetermined surgical structure to be generated in the eye, a light source for illuminating at least the portion of the eye, and a detection device for recording an image of at least the portion of the eye, and to a method for introducing energy into an eye according to a predetermined surgical structure by means of an excimer laser or a femtosecond laser, particularly an operating method for an opthalmological laser treatment device which has a treatment laser and a detection device for recording an image of the eye.

The surgical structure can be predetermined, for example, in the form of irradiation control data sets such as shot position, shot intensity and shot frequency. Alternatively, it may be a matter of more abstract data such as parameterized spatial curves which, as a preliminary step for irradiation control data, describe the incisions to be made. The surgical structure to be generated in the eye may also be represented in any other suitable form. A digital camera, for example, can be used as detection device.

It is noted that citation or identification of any document in this application is not an admission that such document is available as prior art to the present invention.

Ophthalmological laser treatment devices can be used to perform laser surgical procedures on the cornea such as femtosecond lenticule extraction (FLEx), in particular small incision femtosecond lenticule extraction (SMILE). A corresponding femtosecond laser system is described in WO 2008/064771 A1. In this case, the removal of stromal tissue required for refractive correction is separated by a twofold laser cutting for preparing a lenticule. In so doing, the zone of the actual refractive correction (hereinafter: correction zone) is entirely contained within the lenticule, but the lenticule can be greater than the correction zone. The size of the correction zone and the size of the lenticule are so selected depending on optical and physiological factors that the refractive correction in the correction zone does not depend upon the situation in the transition from the edge of the correction zone to the edge of the lenticule. For example, shape matching may be required in this case so as to rule out any contribution to the refractive correction.

The lenticule can then be removed with the help of forceps after opening a corneal flap covering the incision area or, alternatively, through a small lateral laser incision. Only a femtosecond laser system is required for this purpose. Alternatively, it is known, e.g., from US 2006/0155265 A1 to cut a corneal flap using a fs laser system and then to perform refractive corrections in the cornea under the lifted flap using an additional excimer laser. The corneal flap is then closed again.

Another possibility for improving defective vision by laser surgery is known from WO 2006/051364 A1. In this method, deep cuts are made in stromal tissue by a femtosecond laser to produce a contiguous cavity, particularly with a cylindrical shape, without ablation of tissue. When the cavity collapses, the cornea relaxes due to the reduced tissue strength and intraocular pressure and assumes a new shape with altered curvature.

In general, there exists the need for the structure which is to be introduced into the eye by excimer laser or femtosecond laser to be exactly positioned in the coordinate system of the laser. The required accuracy depends on the type of treatment. If there is no correction of aberrations of a higher order than sphere and cylinder, the accuracy requirement with skillfully constituted surgical structure (also referred to as "profile") is low, i.e., about 0.2 mm.

WO 2008/055604 A1 describes how the eye to be treated can be positioned relative to the treatment laser by displacing a support device for the patient by recording monitoring images of the eye and detection of the pupil. For this purpose, the actual position of the pupil is compared with a predetermined reference position and a displacement is calculated, for example, between the actual center and reference center of the pupil. This displacement can either be compensated automatically by a movement of the support device or the operator can be given instructions for a manual compensating movement.

In spite of the displacement compensation, suboptimal treatment can result so that vision is not optimal, particularly in dark environments.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that ate found in the prior art or that affect a basic or novel characteristic of the invention.

It is further noted that the invention does not intend to encompass within the scope of the invention any previously disclosed product, process of making the product or method of using the product, which meets the written description and enablement requirements of the USPTO (35 U.S.C. 112, first paragraph) or the EPO (Article 83 of the EPC), such that applicant(s) reserve the right to disclaim, and hereby disclose a disclaimer of, any previously described product, method of making the product, or process of using the product.

SUMMARY OF THE INVENTION

It is the object of the invention to improve an opthalmological laser treatment device and a method of the type mentioned above so that vision is improved after a laser surgical treatment.

The invention provides an evaluating unit which is adapted to determine an instantaneous degree of overlap between an optical zone of the eye and the structure, or at least a part of the structure effecting refractive correction, based on a recorded image. In connection with treatment of the cornea, the optical zone is the projection of the pupillary aperture (particularly open to the maximum extent) on the cornea or most often generally that region of the tissue to be treated through which light arrives in the eye via the pupillary aperture (particularly open to the maximum extent) and can contribute to imaging. Accordingly, the instantaneous overlap depends upon the degree to which the pupil is open at that instant. Further, according to the invention, the determined degree of overlap can be taken into account in at least the step of determining the irradiation control data and/or the step of deciding to start irradiation of the eye. The degree of overlap can be determined, for example, as a one-dimensional or multi-dimensional value. (scalar, vector or higher-order tensor).

According to the invention, it was recognized that, regardless of the type of positioning (fully automated, semi-automated or manual), by determining the degree of overlap between the (instantaneous) optical zone and the structure to be introduced, or at least the part of the structure effecting refractive correction, the coverage of the optical zone can be monitored by means of the tissue volume that is specifically altered by the laser treatment and accordingly a complete coverage is made possible, which is important for a successful refractive treatment without vision impairment. If there is no monitoring of the overlap, as is the case in the prior art, vision may be impaired under low ambient brightness. When the comparison of the overlap of the pupils and the treatment geometry is carried out automatically, the user can fully concentrate on the task of centering.

The structure to be introduced can involve, for example, a tissue volume (lenticule) to be removed manually following the laser treatment. It can also involve, for example, an incision pattern for radial keratectomy or cylindrical or conical incisions. These structures usually have a center of symmetry which should be positioned approximately in the center of the optical zone. Structures of this kind to be introduced often have no incisions in the center of the structure.

The evaluating unit for determining the degree of overlap preferably determines an area of the pupil based on the recorded image and an area of the structure, or at least of the part of the structure effecting refractive correction, and an intersection between the two areas. The shape and position of the pupil are advisably determined in order to determine the pupil area. The areas can be determined, for example, as scalars (amount of area in question), as plane outline curves, as parameterized spatial vector area or as point clouds of discrete sampling points. Based on the intersection, the degree of overlap can be determined in an economical manner, for example, by determining the quotient from the area size of a plane projection of the intersection and the area size of the pupil. The imaging scale of the recorded image must necessarily be taken into account when determining the areas and the intersection.

The evaluating unit is advantageously adapted to identify and locate a characteristic of the eye in the recorded image and to determine a relative offset between a point of the characteristic and a point of the structure. For example, the pupil, the pupil edge, the area centroid of the pupil, a best-fit circle or a best-fit ellipse can be identified as characteristic. In particular, the offset or an oppositely directed offset of the same magnitude and/or the degree of overlap can be indicated visually and/or acoustically. The offset can advantageously be used in assessing the overlap situation.

In order to allow a sufficient coverage of the optical zone by the surgical structure (hereinafter also referred to as treatment site), the structure to be introduced, for example, edge cuts of a lenticule, can be displaced and/or enlarged particularly until a complete overlapping with the pupil is predicted. This can be carried out manually or in a semi-automated or fully automated manner (by the evaluating unit or a control unit). The enlargement of the treatment site (in this example, the actual correction zone within the lenticule diameter) relative to the optical zone (particularly the maximum pupil diameter) by an amount corresponding at least to the offset of the working center (lenticule center) relative to the center of the optical zone (scotopic pupil center) can be referred to as decentering.

Therefore, it is particularly advantageous when the evaluating unit determines and outputs a degree of suitability of the instantaneous coverage situation between structure and optical zone based on the determined degree of overlap. This makes it easier for the operator to assess the coverage situation and the operator can accordingly reduce the duration of the treatment, which minimizes the likelihood of interim changes in position on the part of the patient.

In preferred embodiment forms, the evaluating unit displays the recorded image visually in superposition with a graphic representation of the structure according to the determined offset. In this way, the operator can interpret the degree of superposition and particularly the coverage situation better and faster overall, which further reduces the treatment time.

It is advisable that a support device is provided for the patient and a positioning device is provided for displacing the support device and/or the laser; the evaluating unit controls the positioning device depending on the determined degree of overlap between the pupil and the structure and/or depending on the offset between the characteristic and the structure. Accordingly, the location at which the structure is generated can be displaced relative to the eye without changing the actual structure to be generated. Only a translation of the structure is carried out in the coordinate system of the laser. This allows an unsatisfactory overlap to be compensated in a semi-automated or fully automated manner and can likewise serve to shorten the treatment time.

In advantageous embodiments the evaluating unit compares a value of the determined degree to a predetermined threshold and outputs a haptic and/or visual and/or acoustic signal depending on a result of the comparison. For example, the operator can be alerted about an acceptable coverage or warned about an insufficient coverage. Alternatively or in addition, the evaluating unit can compare a value of the determined degree with a predetermined threshold value and, depending on a result of the comparison, particularly also depending on a relative offset between a characteristic and the structure, an irradiation of the eye corresponding to the structure can be carried out, particularly when the two threshold values are identical. A comparison of this kind can advisably take place after an offset between laser and eye has been carried out to compensate for an unsatisfactory overlap. Provided the conditions for offset and overlap are met, this allows in particular a fully automated treatment so that the probability of interim changes in position on the part of the patient is minimized.

The eye is preferably illuminated by infrared light. Therefore, the pupil is open to the maximum extent so that the instantaneous optical zone reaches its maximum size. Alternatively, the eye can be illuminated by visible light for recording the image, and an intensity of the light is determined and, based on an instantaneous area of the recorded image and on the intensity, a maximum pupil area is predicted and is used for determining the overlap. Alternatively, when illuminating with visible light maximum pupil dilation can also be achieved through medication, although this will mean a temporary stress for the patient after treatment.

In preferred embodiment forms, the opthalmological treatment device comprises a contact element for mechanically fixating the eye. The contact element, typically a contact glass, is advisably transparent to the spectral region used for the therapeutic radiation. By fixating the eye mechanically, the risk of an erroneous positioning of the surgical structure in the eye can be reduced. The mechanical fixation is required particularly with femtosecond lasers.

The degree of instantaneous overlap can advantageously be determined before and/or after implementing the mechanical fixation. Determining the degree of overlap prior to fixation can assist in determining a shifting of the patient necessary for achieving a specified degree of overlap. To this end, for example, a degree of overlap can be predicted as a function of an offset by means of a computer simulation based on a mathematical model. That offset for which a maximum of the degree of overlap is predicted can be determined subsequently, for example. Shifting of the patient followed by fixation of the eye can then be carried out automatically, for example, or only when actuated by the operator. Alternatively, the shifting of the patient can be presented to the operator merely as a suggestion. The operator must then initiate the fixation manually.

The corneal limbus is suitable as a definitive reference for eye movement tracking with respect to the cornea. If it is not visible, only the pupil remains as principal geometric feature. However, the variability of pupil size presents a drawback in this regard. As the size changes, the center of the pupil also shifts. Therefore, it is advantageous to track movements of the limbus during and/or after the process of anchoring to the contact element, since the limbus is in a fixed relationship to the eye geometry. In particular, if the position of the photopic and scotopic pupil center in relation to the limbus is known, the position of the scoptopic pupil can be determined for any pupil diameter by interpolation and the overlap can be evaluated on that basis.

The invention also comprises a control unit which is set up to implement a method according to the invention. The setup can be carried out in a programmed manner, for example, by means of software modules for determining a degree of an instantaneous overlap between an optical zone of the eye and the structure based on the recorded image and for determining irradiation control data and/or for deciding about beginning irradiation of the eye depending on the degree determined.

The invention is provided not only for application to the cornea, but can be applied to all parts of the anterior portion of the eye, for example, to the eye lens or the capsular bag.

DETAILED DESCRIPTION OF EMBODIMENTS

It is to be understood that the figures and descriptions of the present invention have been simplified to illustrate elements that are relevant for a clear understanding of the present invention, while eliminating, for purposes of clarity, many other elements which are conventional in this art. Those of ordinary skill in the art will recognize that other elements are desirable for implementing the present invention. However, because such elements are well known in the art, and because they do not facilitate a better understanding of the present invention, a discussion of such elements is not provided herein.

The present invention will now be described in detail on the basis of exemplary embodiments.

Figure 1A:
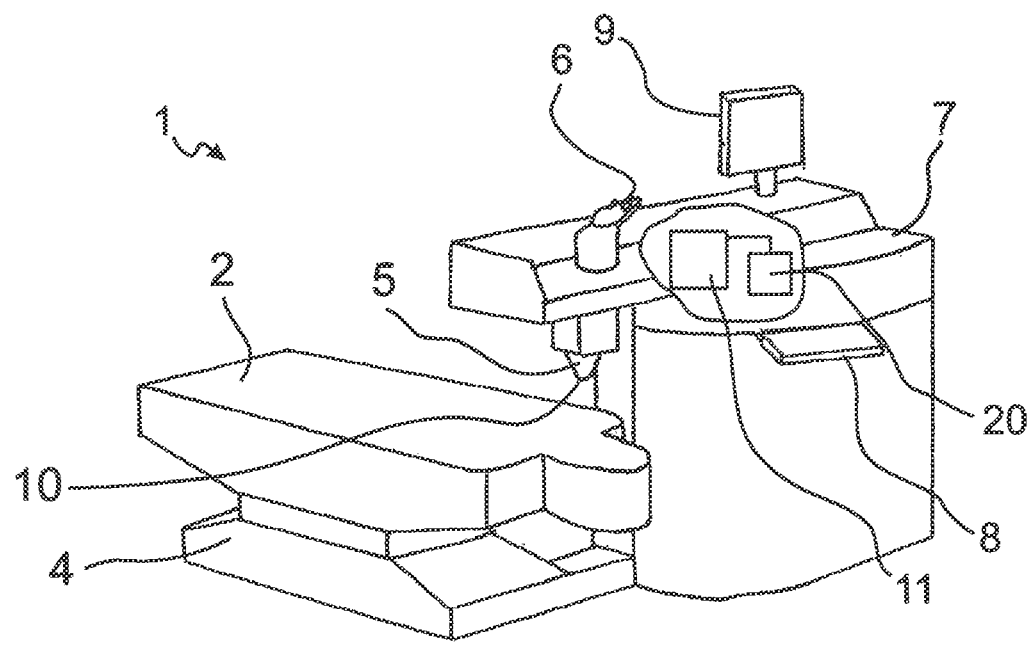
FIG. 1 shows an ophthahnological laser treatment device.

FIG. 1 shows an opthalmological laser treatment device 1 for correcting defective vision using laser radiation. The outer appearance is shown schematically in FIG. 1A. The treatment device 1 comprises a support device 2 for a patient in the form of a table and a treatment laser 3 having optics for positioning and focusing the laser beam in the area of a treatment position at which a patient's eye can be positioned. It further comprises a positioning device 4 which supports the table 2 and can move it linearly in all three spatial directions. A microscope beam path which allows the operator to visually monitor the course of the treatment in an observation eyepiece 6 is coupled into the beam path of the treatment laser 3 exiting the treatment head 5 which is arranged above the table 2.

The treatment device 1 further comprises as control unit 7 a computer having a keypad 8 and a monitor as display 9. The opthalmological device 1 is controlled by means of the control unit 7. The laser 3 is a femtosecond laser, for example, so that a flap or a lateral extraction incision and a lenticule can be cut by the same laser. At its end facing the table 2, the treatment head 5 has a contact element 10 in the form of a contact glass which touches the eye of the patient during treatment and is spatially fixed relative to the treatment device 1. During the irradiation process, the laser beam is focused in the eye of the patient through the contact element 10. For example, the contact element 10 can be plane or anatomically curved on the side facing the eye.

In alternative embodiment forms, an excimer laser can be provided instead of or in addition to the femtosecond laser. When an excimer laser is used exclusively, a contact element 10 can be dispensed with. A movement tracking system which repositions the treatment laser 3 to track possible eye movements of the patient during the irradiation process is advisable when using an excimer laser.

Figure 1B:
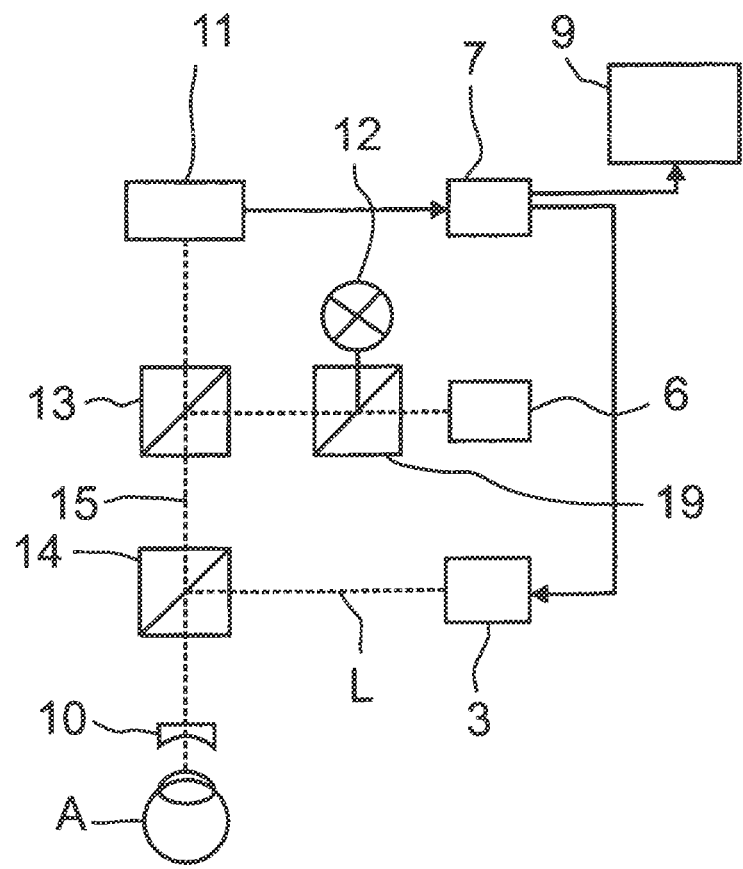

FIG. 1B shows the coupled beam paths of the treatment laser 3, microscope 6, detection device 11 and light source 12 schematically and in a highly simplified manner with respect to the optical construction. The detection device 11 is constructed as a camera by which the eye A of the patient is recorded through two beamsplitters 13, 14 and the contact glass 10 which is shown here at a distance from the eye A. Therefore, an observation beam path 15 runs from the eye A through the contact glass 10 and both beamsplitters 13 and 14 to the camera 11. The image taken by the camera 11 is sent to the computer 7. Beamsplitter 13 allows the eye A to be observed microscopically via the observation eyepiece 6. The treatment laser beam L can be directed from the laser 3 to the eye A via beamsplitter 14 when the eye A is spatially fixated by means of the contact glass 10 in order to carry out the desired correction of defective vision.

The light source 12 preferably emits exclusively infrared radiation because in this case the pupil can open wide and, in addition, a high-contrast video recording of the pupil can be carried out, particularly also when the iris is very dark. Alternatively or in addition, however, the light source 12 can also emit visible light. In particular, the visible spectral component can be cut off by means of a filter (not shown). The light of light source 12 is reflected into the microscope beam path by another beamsplitter 19, for example.

When the patient's eye is detected through the device 7, preferably during the process of contacting the contact element 10 or immediately thereafter, the video image of the camera 11 is analyzed by the evaluating unit 20. To this end, it carries out a detection of the pupil and displays at least one geometric characteristic, for example, the pupil edge, area centroid, best circular fit or best elliptical fit, to the user on the monitor 9 and/or in the eyepiece 6 in superposition with the video image. In addition or alternatively, it compares a geometric characteristic with at least one treatment parameter, for example, the lenticule position, the position and shape of the correction zone of the lenticule, the lenticule diameter, the cutting angle, the flap diameter, the center of the flap, the position of the flap hinge, or the angle of the hinge, and/or a system parameter, e.g., the center of the treatment site, and determines a deviation from a predetermined ideal case and displays this on the monitor 9.

For example, when analysis is carried out by determining the area ratios of the pupil and correspondingly scaled surgical structure, a degree of overlap between the structure to be generated, or at least the part of the structure effecting refractive correction, and the optical zone and a shift between the center of the pupil as exemplary reference point and the center of the structure to be generated are determined. This can be used to control the positioning device 4 in such a way that the table 2 and, therefore, the eye A of the patient lying on the table 2 can be moved into a predetermined reference position relative to the contact glass 2. Alternatively, instead of the pupil center, any other eye-based characteristic can be used to determine the displacement by identifying and locating it in the recorded image. Reference is made to WO 2008/055604 A1, particularly FIG. 3 and the accompanying remarks, with respect to the description of the determination of displacement. The image recording and the identification and locating of the characteristic are advisably carried out repeatedly so as to allow for changes in position of the eye. This also applies to the determination of the instantaneous degree of overlap.

The area can be determined, for example, by counting picture elements (pixels) in digitalized images, for example, the pixels in the intersection set between determined pupil margin curves and the correction zone of the surgical structure. The ratio of the surface area of the total pupil area to the proportion of the pupil area coinciding with the correction zone gives the degree of overlap. This degree of overlap is 100% when the pupil is located completely within the correction zone. Further, the deviation of the centroids from the correction zone and pupil area, which gives information about the overlap reserve (additional overlapping of the correction zone beyond the pupil area), can be used for the degree of suitability. However, it is also conceivable to output a signal for a sufficient suitability already when there is a partial overlap of only 90% or 95%, for example.

The accuracy of the comparison between treatment parameters and characteristic geometric quantities of the video image can be further improved through additional adaptation of the scaling of the video image and/or overlapped visualized treatment parameters. The scaling provides for improved geometric congruency of the metric of the coordinate systems to be compared. Further, the deviation can be evaluated particularly on the basis of whether the current position does not exceed a given threshold value for the decentering and/or a given threshold value for the overlap between the optical zone and the structure to be generated.

For example, the evaluating unit. 20 which is a software module of the control unit 7, for example, displays on the monitor 9 the last image recorded in which the detected characteristic, in this case the edge of the pupil, is marked and the structure to be generated is superimposed. Optionally, the structure to be generated and the marking of the detected characteristic can also be reflected into the microscope beam path so that the operator sees these criteria directly superposed with the image of the eye A. In this way, the operator himself can see the degree of overlap directly.

In a special embodiment, an automatic response of the device, for example, a compensation of the detected displacement, can be initiated based on the evaluation.

Figure 2:
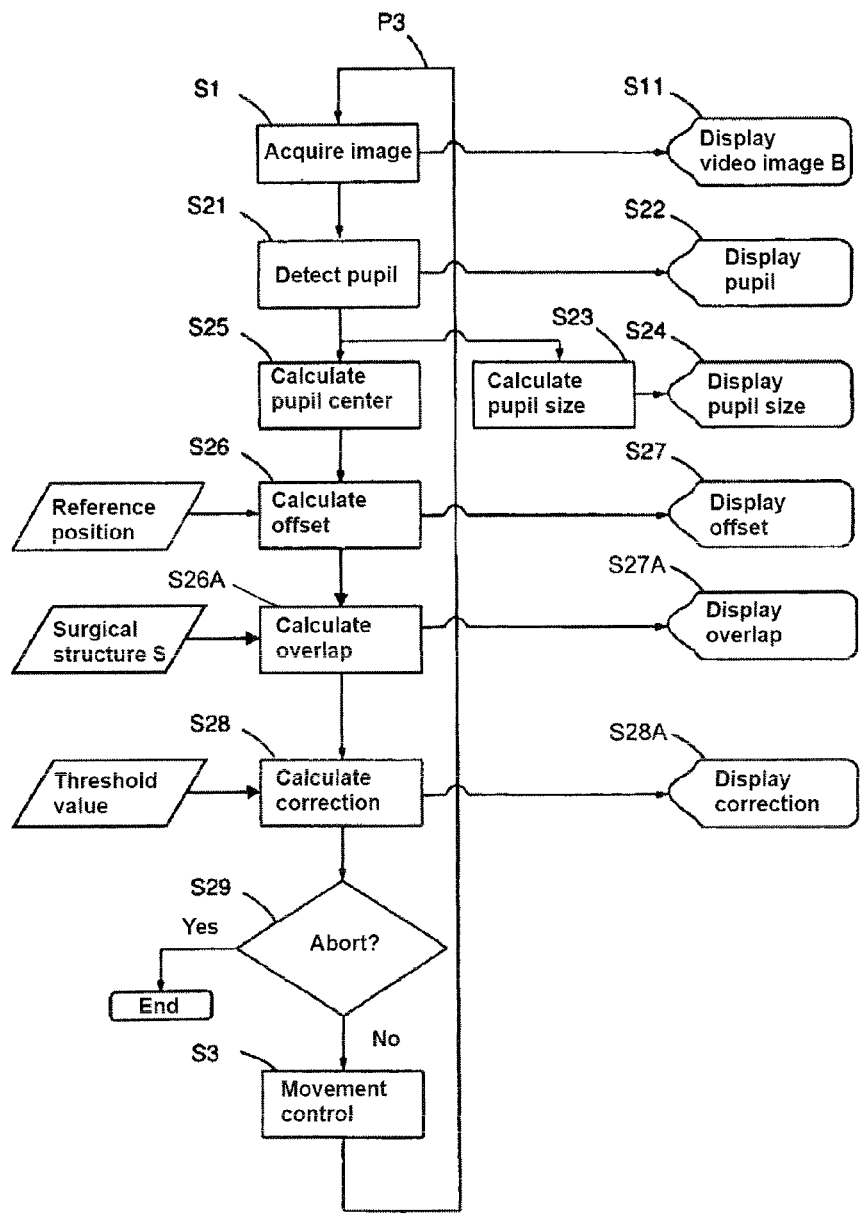
FIG. 2 shows a flowchart for a method for controlling a compensating movement.

The sequence of a method for movement control is shown schematically by way of example in the form of a flow chart in FIG. 2. The steps substantially correspond to those described in WO 2008/055604 A1, wherein the display data in steps S11, S22, S24 and S27 are displayed simultaneously.

For example, the detected pupil and the determined displacement are superimposed on the video image in identical scale and the rest of the data are displayed alongside. Steps S26A, S27A and S28A which will be described in the following are carried out in addition. In so doing, the structure to be generated is likewise superimposed with the video image in the course of step S27A for displaying overlapping. As in WO 2008/055604 A1, the display can also be carried out additionally or alternatively in the eyepiece 6; the video image is omitted in the eyepiece 6 because the optical image is available therein.

In step S26A, the instantaneous degree of overlap between the structure S and the instantaneous optical zone of the eye A is determined based on the detected pupil as geometric characteristic and based on the predetermined surgical structure S and is displayed, for example, by shading of the intersection between the areas of the structure S projected into the video image and the detected pupil P. The degree of overlap compared to a predetermined threshold value can be used in the calculation of the correction in step S28. The threshold value describes, for example, a minimum overlap to be achieved. If this can be achieved without movement, the process is aborted. Otherwise, the determined suggested correction is shown in step S28A with the other data, for example, as a displacement vector in the video image.

As an alternative to a fully automatic compensation movement, a signal can also be displayed to the user. The signal can be haptic, optical or acoustic. In particular, there is provided a quantitative indication of the degree of deviation found, particularly a simultaneous video superposition of the detected pupil and the expected treatment geometry, for example, the lenticule diameter, flap diameter or the centers.

The invention can also be used in excimer laser systems in which the change in shape of the cornea is carried out by ablation of the cornea. In this case, the object is not to position the patient in relation to the therapy optics with high precision, since the therapeutic device usually compensates for slight inaccuracies in positioning by adjusting the beam position by an amount of deviation measured by movement tracking; however, the comparison in terms of shape and position between the shape and/or size of the detected pupil and the surgical structure to be implemented an ablation pattern in the case of excimet lasers—can also be used in treatment methods of this kind to improve the reliability and efficiency of the treatment. In this case again, it is useful to omit illumination in the visible spectral region and to use infrared illumination in order to correctly detect the optical zone applicable to the night vision of the patient.

In another embodiment, other features of the eye are also detected, for example, iris structures. They are used to compare the relative rotational position of the eye with similar information from diagnostic measurements in order to determine relative rotation and relative displacement in relation to a diagnostic image (register image) in this way.

In another embodiment, this information is used to carry out a rotation and/or displacement of the treatment geometry so as to compensate for the relative rotation and/or displacement found in relation to diagnostic measurements.

In another embodiment, the detected features of the eye are compared to known features of the eye of the scheduled patient to check the identity of the eye to be treated (eye recognition). In this case, the probability of a mistake or the degree of identity found is displayed to the user.

Figure 3A:
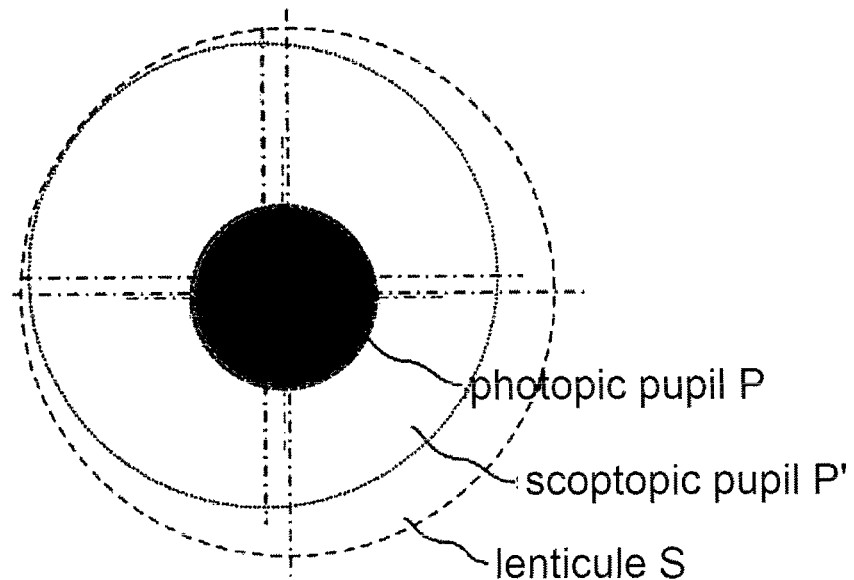
FIG. 3 shows variants for centering a lenticule.
Corresponding parts have the same reference numerals in all of the drawings.
Figure 3B:
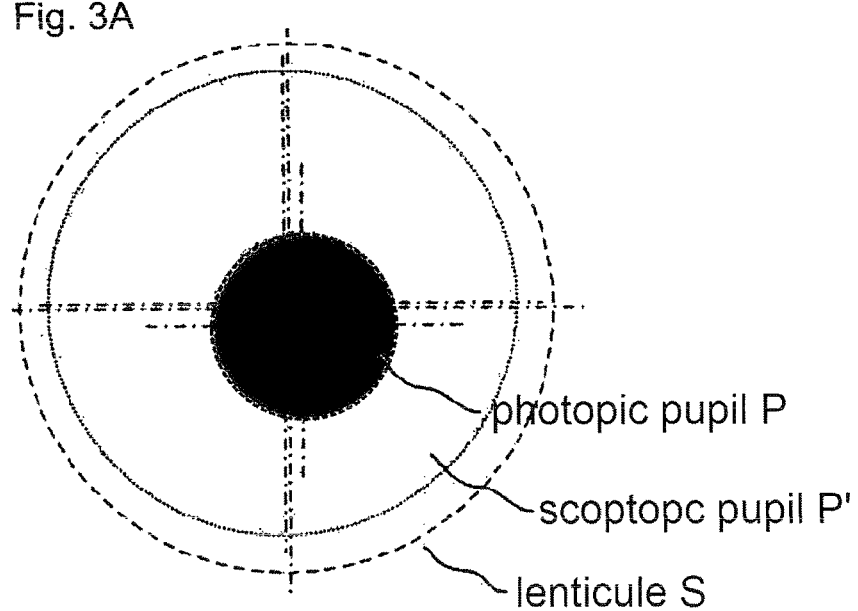

FIG. 3 shows two variants for centering a lenticule as structure S to be generated: near the center of the photopic pupil P in FIG. 3A and near the center of the scotopic pupil P' in FIG. 3B. It will be seen that in case A the lenticule and scotopic pupil P' just barely overlap. When availed of the inventive solution, the operator will be able to make an exact evaluation of these and similar situations in the available time.

For a description of the generation of the laser beam, reference is had to WO 2008/055604 A1, particularly FIGS. 6 and 7 and the accompanying description.

While this invention has been described in conjunction with the specific embodiments outlined above, it is evident that many alternatives, modifications, and variations will be apparent to those skilled in the art. Accordingly, the preferred embodiments of the invention as set forth above are intended to be illustrative, not limiting. Various changes may be made without departing from the spirit and scope of the inventions as defined in the following claims.

LIST OF REFERENCE NUMERALS 1 laser treatment device
2 support device
3 treatment laser
4 positioning device
5 treatment head
6 observation eyepiece
7 control unit
8 keypad
9 monitor
10 contact element
11 detection device
12 light source
13 beamsplitter
14 beamsplitter
15 observation beam path
19 beamsplitter
20 evaluating unit
A eye
B video image
P pupil
S surgical structure

The invention claimed is:

1. An opthalmological laser treatment device comprising:
a treatment laser configured to introduce energy into a portion of an eye of a patient according to a predetermined surgical structure;
a light source configured to illuminate at least the portion of the eye;
a detection device configured to record an image of at least the portion of the eye; and
an evaluating unit which is programmed to:
determine an area of an optical zone of the eye based on a recorded image and determine an area of the predetermined surgical structure; and
determine a degree of an instantaneous overlap between the optical zone of the eye and the predetermined surgical structure based on the recorded image,
wherein the evaluating unit is programmed to determine an area of a pupil based on the recorded image and the area of the predetermined surgical structure and an intersection between the two areas.

2. The opthalmological treatment device according to claim 1;
Wherein the evaluating unit is configured to identify and locate a characteristic of the eye in the recorded image and to determine a relative offset between a point of the characteristic and a point of the predetermined surgical structure.

3. The opthalmological treatment device according to claim 2;
wherein the evaluating unit displays the recorded image visually in superposition with a graphic representation of the predetermined surgical structure according to the determined offset.

4. The opthalmological treatment device according to claim 1, further comprising:
a support device for the patient and a positioning device configure to displace the support device and/or the laser;
wherein the evaluating unit controls the positioning device depending on the determined degree of overlap between the pupil and the predetermined surgical structure.

5. The opthalmological treatment device according to claim 1;
wherein the evaluating unit compares a value of the determined degree of overlap to a predetermined threshold and outputs a haptic and/or visual and/or acoustic signal depending on a result of the comparison; and/or
wherein the evaluating unit compares a value of the determined degree of overlap to a predetermined threshold value and, depending on a result of the comparison, carries out an irradiation of the eye corresponding to the predetermined surgical structure.

6. The opthalmological treatment device according to claim 1, further comprising:
a contact element for mechanically fixating the eye.

7. A method for introducing energy into an eye according to a predetermined surgical structure by means of an excimer laser or a femtosecond laser, the method comprising the following steps:
determining with an evaluation unit, based on a recorded image, an area of an optical zone of the eye based on a recorded image and determining an area of the predetermined surgical structure, and
determining with the evaluation unit a degree of instantaneous overlap between the optical zone of the eye and the predetermined surgical structure,
wherein at least the determining the degree of instantaneous overlap comprises identifying a pupil in the recorded image; and
determining an area of the pupil based on the recorded image and determining the area of the predetermined surgical structure and then determining an intersection of the two areas; and
taking the determined degree of instantaneous overlap into account in at least one of:
a step of determining irradiation control data; and
a step of deciding on a commencement of irradiation of the eye.

8. The method according to claim 7;
Comprising:
Recording an image of the eye by means of a detection device.

9. The method according to claim 8:
wherein the eye is illuminated with infrared light, or wherein the eye is illuminated with visible light for recording the image; and
wherein an intensity of the light is determined and, based on an instantaneous area of the recorded image and on the intensity, a maximum pupil area is predicted and is used for determining the overlap.

10. The method according to claim 7;
Wherein the predetermined surgical structure is displaced and/or enlarged until a complete overlapping with the pupil is predicted.

11. The method according to claim 7;
Wherein the eye is mechanically fixated.

12. The method according to claim 11;
Wherein the degree of instantaneous overlap is determined before and/or after the mechanical fixating is carried out.

13. A control unit configured to implement the method according to claim 7.

14. The opthalmological treatment device according to claim 1;
Wherein the predetermined surgical structure has a center of symmetry in which there are no locations to be irradiated.

15. The opthalmological treatment device according to claim 2, further comprising:
A support device for the patient and a positioning device configured to displace the support device and/or the laser;
Wherein the evaluating unit controls the positioning device depending on the offset between the characteristic and the predetermined surgical structure.

16. The method according to claim 7;
Wherein the predetermined surgical structure has a center of symmetry in which there are no locations to be irradiated.

17. The opthalmological treatment device according to claim 1;
Wherein the portion of the eye treatment laser is configured to introduce energy into is a cornea of the eye.

18. The opthalmological treatment device according to claim 1;
Wherein the predetermined surgical structure is a lenticule to be removed manually.

19. The opthalmological treatment device according to claim 1;
Wherein the evaluating unit is configured to determine a lateral overlap as the overlap.

20. The method according to claim 7;
wherein the portion of the eye laser introduces energy into is a cornea of the eye.

21. The method according to claim 7;
wherein the predetermined surgical structure is a lenticule to be removed manually.

22. The method according to claim 7;
determining the overlap laterally.

* * * * *